(12) United States Patent
Masaki (10) Patent No.: US 8,944,603 B2
(45) Date of Patent: Feb. 3, 2015

(54) OPHTHALMOLOGIC APPARATUS

(75) Inventor: Toshifumi Masaki, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/558,176

(22) Filed: Jul. 25, 2012

(65) Prior Publication Data

US 2013/0027667 A1 Jan. 31, 2013

(30) Foreign Application Priority Data

Jul. 29, 2011 (JP) .................................. 2011-167052

(51) Int. Cl.
*A61B 3/12* (2006.01)
*A61B 3/14* (2006.01)

(52) U.S. Cl.
CPC ........................................ *A61B 3/14* (2013.01)
USPC ............ 351/221; 351/205; 351/206; 351/207

(58) Field of Classification Search
USPC ................... 351/201–204, 215–218
See application file for complete search history.

(56) References Cited

U.S. PATENT DOCUMENTS 4,786,162 A * 11/1988 Fujiwara et al. .............. 351/206
2011/0051086 A1 3/2011 Takai et al.

FOREIGN PATENT DOCUMENTS

| JP | 60-190930 A | 9/1985 | |
| JP | 60190930 | * 9/1985 | ............... A61B 3/12 |
| JP | 10179522 A | 7/1998 | |

* cited by examiner

*Primary Examiner* — Ricky Mack
*Assistant Examiner* — William Alexander
(74) *Attorney, Agent, or Firm* — Canon USA, Inc. IP Division (57) ABSTRACT

An ophthalmologic apparatus includes an integration unit configured to integrate a light emission amount of a light source for illuminating a subject's eye, a comparison unit configured to compare an integration value by the integration unit with a first reference value, and an initialization unit configured to initialize the integration value if the integration value exceeds the first reference value as the comparison result by the comparison unit.

18 Claims, 8 Drawing Sheets

| LIGHT AMOUNT (LEVEL) | INTEGRATION CIRCUIT OUTPUT VOLTAGE (V) | REFERENCE D/A VALUE | |
|---|---|---|---|
| 2.0 | 20.0 | 1020 | STANDARD AUTOFLUORESCENCE |
| 1.5 | 14.1 | 721 | |
| 1.0 | 10.0 | 510 | MINIMAL AUTOFLUORESCENCE |
| 0.5 | 7.1 | 361 | |
| 0.0 | 5.0 | 255 | MAXIMAL COLOR |
| -0.5 | 3.5 | 180 | |
| -1.0 | 2.5 | 128 | |
| -1.5 | 1.8 | 90 | |
| -2.0 | 1.3 | 64 | STANDARD COLOR |
| -2.5 | 0.9 | 45 | |
| -3.0 | 0.6 | 32 | |
| -3.5 | 0.4 | 23 | |
| -4.0 | 0.3 | 16 | MINIMAL COLOR |

OPHTHALMOLOGIC APPARATUS

BACKGROUND OF THE INVENTION

1. Field of the Invention

The present invention relates to an ophthalmologic apparatus.

2. Description of the Related Art

In a conventional ophthalmologic apparatus such as a fundus camera, a xenon tube or the like is used for a light source for capturing an image of a fundus of a subject's eye. Since the light source generally degrades with time, an amount of the imaging light changes even when the light emission of the light source is normally stopped at the same timing.

Therefore, in order to control the imaging light amount, the light reflected from the subject's eye is monitored by a light receiving element such as a photodiode, and the output of the light receiving element is integrated by an integration circuit equipped with an operational amplifier and a capacitor. Then, there is a known technique of controlling the imaging light amount in a manner such that the light emission is stopped when the output voltage of the integration circuit becomes larger than a reference voltage based on the comparison between the output of the integration circuit and the reference voltage. In addition, there is a known technique of changing the imaging light amount according to the sensitivity of a film to be used for an imaging operation or the interest of an examiner for an imaging region by changing the reference voltage (see Japanese Patent Application Laid-Open No. 60-190930).

However, an available range of the reference voltage is limited by the power supply voltage of the circuit for generating the reference voltage. For example, in a case where the light emission of the light source needs to be stopped when the output of the integration circuit becomes 20 V in the imaging operation requiring a high light amount, if the available range of the reference voltage is 0 to 5 V, the light emission of the light source is stopped when the output of the integration circuit exceeds 5 V and the light amount may not be adjusted. In the above-described example, the power supply voltage of the integration circuit is ignored in order to help the understanding. As described above, there is an issue that the light amount may not be adjusted due to the relation between the reference voltage and the output of the integration circuit.

SUMMARY OF THE INVENTION

Aspects of the present invention are directed to a technique capable of adjusting a light amount regardless of a relation between a reference voltage and an output of an integration circuit. The present invention is not limited to the above-described object, and aspects of the present invention are also directed to obtaining functions and effects which are obtained by the respective configurations illustrated in exemplary embodiment to be described below and are not obtained by the conventional art.

According to an aspect of the present invention, an ophthalmologic apparatus includes an integration unit configured to integrate a light emission amount of a light source for illuminating a subject's eye, a comparison unit configured to compare an integration value by the integration unit with a first reference value, and an initialization unit configured to initialize the integration value if the integration value exceeds the first reference value as the comparison result by the comparison unit.

According to aspects of the present invention, the light amount may be adjusted regardless of the relation between the reference voltage and the output of the integration circuit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

An exemplary embodiment according to an ophthalmologic apparatus of the present invention will be described below referring to FIGS. 1 to 8.

Figure 1:
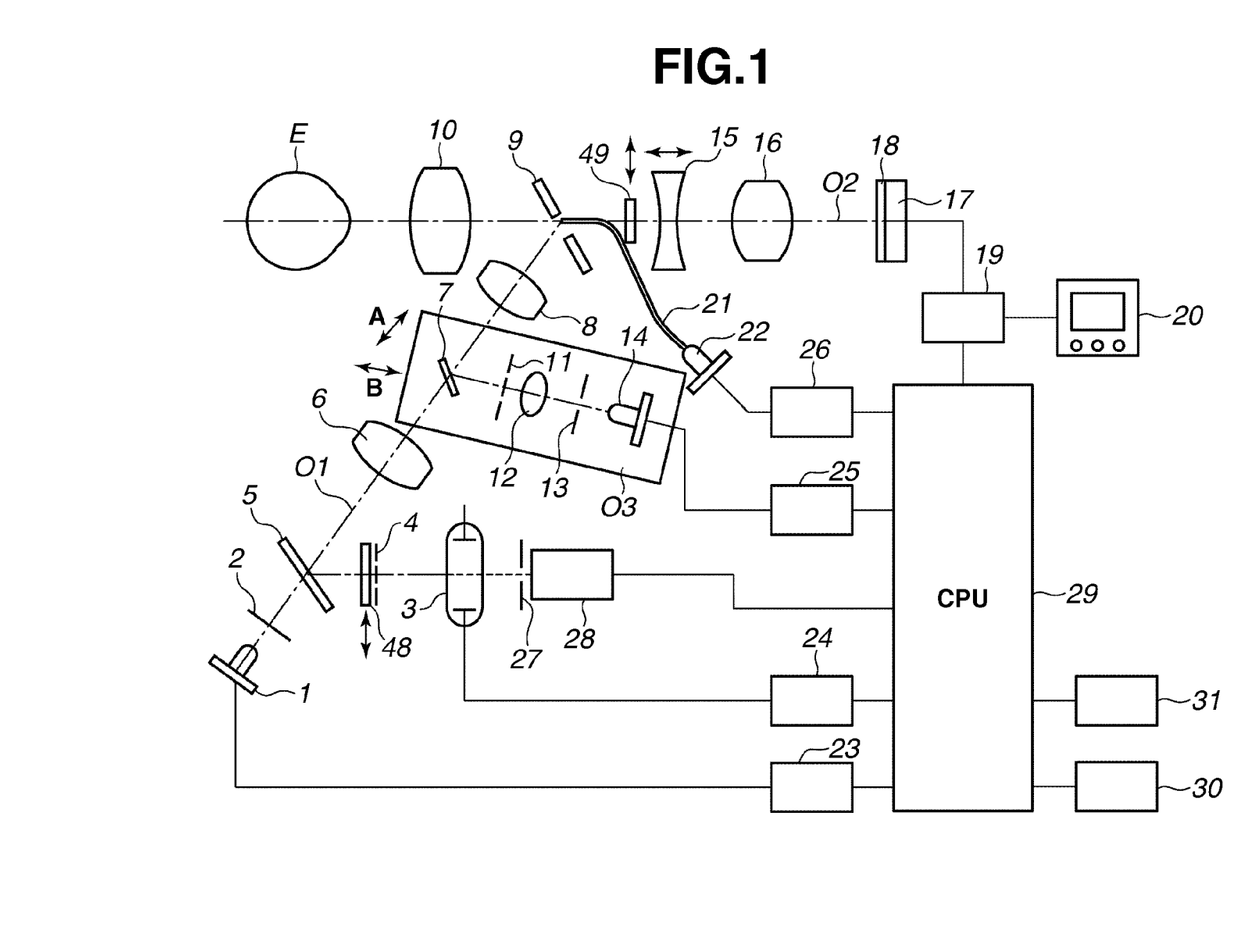
FIG. 1 illustrates an example of a configuration of a fundus camera.

FIG. 1 illustrates an example of a configuration of a fundus camera (ophthalmologic apparatus) of the present exemplary embodiment. On an optical path from an infrared light emitting diode (LED) 1 serving as an infrared observation light source to an objective lens 10, a diaphragm 2 including an annular opening, a dichroic mirror 5 allowing infrared light to be transmitted therethrough and visible light to be reflected therefrom, a relay lens 6, a mirror 7, a relay lens 8, and a perforated mirror 9 are sequentially arranged.

On an optical path from a xenon tube 3 serving as an imaging light source for emitting visible light to the objective lens 10, a diaphragm 4 including an annular opening, the dichroic mirror 5, the relay lens 6, the mirror 7, the relay lens 8, and the perforated mirror 9 are sequentially arranged. The relay lens 6, the mirror 7, the relay lens 8, and the perforated mirror 9 constitute a fundus illumination optical system O1.

An autofluorescence imaging excitation filter 48 is disposed between the diaphragm 4 and the dichroic mirror 5. The autofluorescence imaging excitation filter can be retracted to the outside of the optical axis by a driving system (not illustrated), and is retracted to the outside of the optical axis when color imaging is performed.

In the reflection direction of the mirror 7, a diaphragm 11, a lens 12, a focusing index 13, and an infrared LED 14 serving as a focusing index light source are arranged, which constitutes a focusing index projection optical system O3.

The focusing index projection optical system O3 moves in the direction of the optical axis (a direction A in the drawing) by interlocking with a focusing lens 15. When a still image is captured, the focusing index projection optical system O3 is moved in a direction (a direction B in the drawing) deviating from the optical axis by a driving system (not illustrated) so as to be retracted from the illumination optical system O1.

On an optical path in the transmission direction of the perforated mirror 9, the focusing lens 15, an shooting lens 16, and an imaging unit 17 are arranged, which constitutes a fundus imaging optical system O2. An output of the imaging unit 17 is sequentially connected to an image signal processing unit 19 and a display unit 20. An infrared LED 22 serving as an aligning index light source is connected to the perforated mirror 9 via an optical fiber 21. An inhibition filter 49 for autofluorescence imaging is disposed between the perforated mirror 9 and the focusing lens 15. The inhibition filter 49 can be retracted to the outside of the optical axis by a driving system (not illustrated), and is retracted to the outside of the optical axis when color imaging is performed.

Filters 18, in which three colors of red (R), green (G), and blue (B) filters are arranged in a mosaic shape, are arranged on respective pixels of the imaging unit 17, and the R filter may allow infrared light to be transmitted therethrough. Each pixel has sensitivity for the light of any one of R, G, and B, and the R pixel also has sensitivity for infrared light.

When infrared observation is performed, the image signal processing unit 19 generates monochrome moving image data using an output of the R pixel and outputs a moving image to the display unit 20. When a color still image is captured, the image signal processing unit 19 generates a color still image using outputs of the respective pixels of R, G, and B. When autofluorescence imaging is performed, the image signal processing unit 19 generates a monochrome still image by a predetermined image process using the outputs of the respective pixels of R, G, and B. The generated image is recorded in a recording unit 31 via a central processing unit (CPU) 29.

The infrared LED 1 is connected to an LED driving circuit 23. The imaging xenon tube 3 is connected to a xenon tube driving circuit 24. The infrared emission LED 14 is connected to an LED driving circuit 25. The infrared LED 22 is connected to an LED driving circuit 26. The LED driving circuit 23, the xenon tube driving circuit 24, the LED driving circuit 25, the LED driving circuit 26, a light amount detection unit 28, the imaging unit 17, the image signal processing unit 19, the operation unit 30, and the recording unit 31 are respectively connected to the CPU 29.

The LED driving circuit 23 controls the driving of the infrared LED 1 based on an instruction from the CPU 29. The xenon tube driving circuit 24 controls the driving of the xenon tube 3 based on an instruction from the CPU 29. The LED driving circuit 25 controls the driving of the infrared emission LED 14 based on an instruction from the CPU 29. The LED driving circuit 26 controls the driving of the infrared LED 22 based on an instruction from the CPU 29.

The light amount detection unit 28 is disposed in rear of the xenon tube 3, and is configured to receive a part of the light flux exiting from the xenon tube 3 via a diaphragm 27. More specifically, the light amount detection unit 28 is disposed on an optical axis opposite to the optical axis direction in which the light exiting from the xenon tube 3 is directed toward a subject's eye E. The light amount detection unit 28 detects an amount of the light exiting from the xenon tube 3. The diaphragm 27 includes a transmission portion which is provided on the optical axis of the xenon tube 3 so that light is transmitted therethrough. The portion other than the transmission portion of the diaphragm is configured to reflect, for example, the light exiting from the xenon tube 3 to the opposite side of the subject's eye toward the subject's eye. For example, aluminum or the like is vapor-deposited on the diaphragm 27 so as to reflect light.

Figure 2:
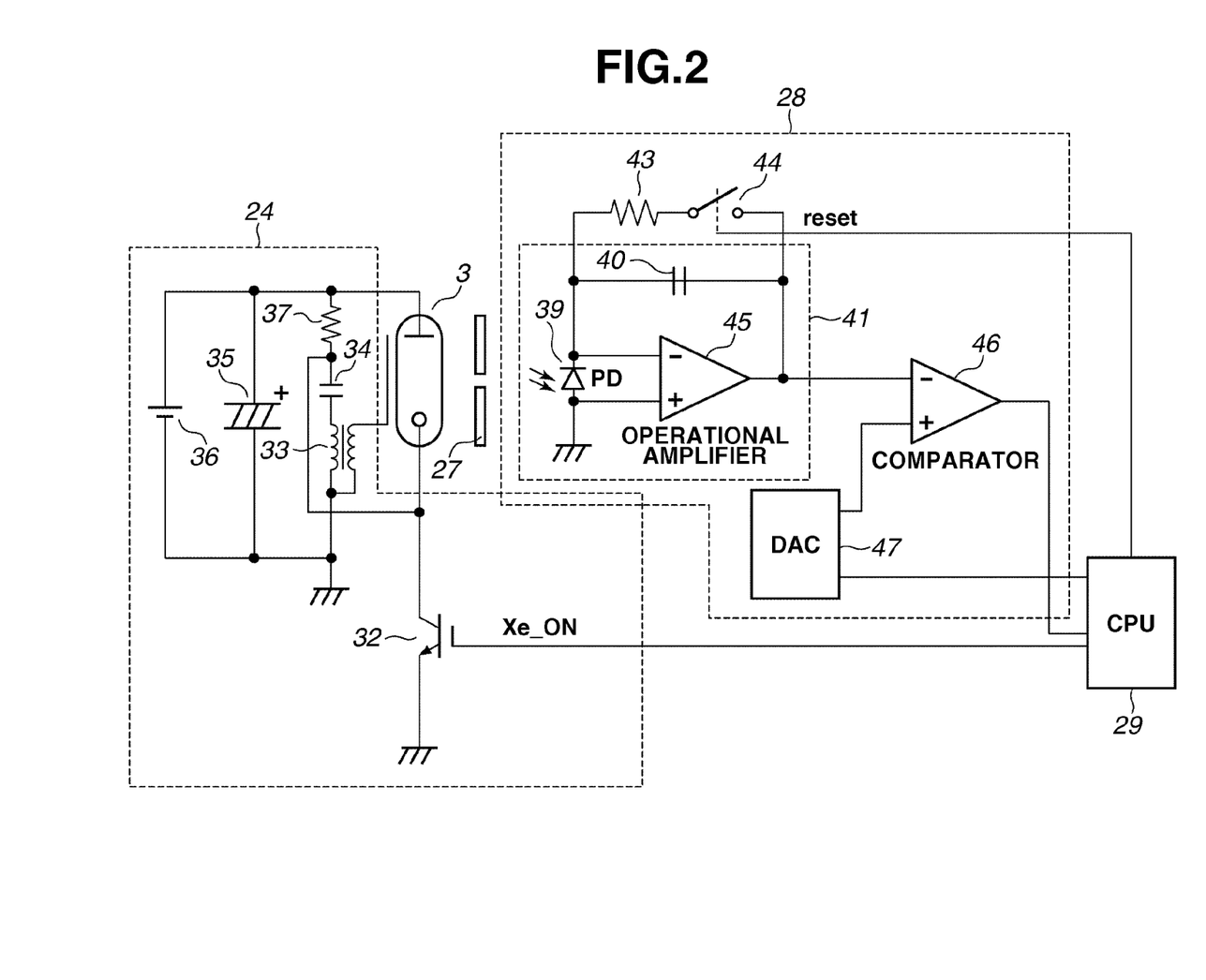
FIG. 2 illustrates an example of an electric circuit of a xenon tube driving circuit and a light amount detection unit.

FIG. 2 illustrates an example of a configuration of an electric circuit of the xenon tube driving circuit 24 and the light amount detection unit 28. The xenon tube driving circuit 24 includes an insulated gate bipolar transistor (IGBT) 32, a trigger transformer 33, a trigger capacitor 34, a main capacitor 35, a power supply 36, and a resistor 37. The main capacitor 35 is charged to a high voltage (for example, 300 V) by the power supply 36. The trigger capacitor 34 is also charged by the power supply 36 via the resistor 37.

When the CPU 29 sets a Xe_ON signal as a control signal for controlling the light emission of the xenon tube 3 to a high level (Hi), the IGBT 32 is turned on, in other words, the IGBT 32 becomes a conducting state, and the electric charges of the trigger capacitor 34 are discharged. Due to the discharge of the electric charges, a current flows to a coil on the left side of the trigger transformer 33. When the current flows to the coil on the left side of the trigger transformer 33, a high voltage is generated in a coil on the right side of the trigger transformer 33, a trigger is input to the xenon tube 3, and a current flows from the main capacitor 35 to the xenon tube 3. When the current flows to the xenon tube 3, the light emission of the xenon tube 3 is started. When the CPU 29 sets the Xe_ON signal to a low level (Low) after the light emission is started, the IGBT 32 is turned off, in other words, the IGBT 32 becomes a non-conducting state, and the current flowing from the xenon tube 3 is interrupted, so that the light emission is stopped.

In this way, the CPU 29 controls the light emission of the xenon tube 3. More specifically, the xenon tube driving circuit 24 controls the light emission of the xenon tube 3 based on the control signal transmitted from the CPU 29.

The light amount detection unit 28 includes an integration circuit 41, a reset resistor 43, an analog switch 44, a comparator 46, and a digital-to-analog (D/A) converter 47. The integration circuit 41 includes a photodiode 39, an integration capacitor 40, and an operational amplifier 45.

The integration circuit 41 outputs a voltage in response to (for example, in proportion to) the light amount of the xenon tube 3 since the integration capacitor 40 is charged by the photoelectric current which is generated in response to (for example, in proportion to) the light amount of the xenon tube 3 and flowing to the photodiode 39. Thus, the integration circuit 41 integrates the current of the photodiode 39. In other words, the integration circuit 41 integrates the light emission amount of the xenon tube 3. In other words, the integration circuit 41 corresponds to an example of an integration unit which integrates a light emission amount of the light source illuminating the subject's eye.

When the CPU 29 turns on the analog switch 44 by outputting, for example, a Hi signal to the analog switch 44, the electric charges of the integration capacitor 40 may be reset via the reset resistor 43. The reset resistor 43 may not be provided. The analog switch is, for example, a metal oxide semiconductor (MOS) switch or the like.

The photodiode 39 is provided on the optical axis of the xenon tube 3 in the direction opposite to the direction directed from the xenon tube 3 toward the subject's eye E. In other words, the photodiode 39 corresponds to an example of a photodiode which is provided on the optical axis of the light source in the direction opposite to the direction directed from the light source toward the subject's eye. The xenon tube 3 is optimized so as to illuminate the subject's eye E, and the light amount other than the optical axis of the light source is unstable. For this reason, since the light amount may be detected on the optical axis of the xenon tube 3 by disposing the photodiode 39 as described above, the light amount can be stably detected.

Based on the control of the CPU 29, the D/A converter 47 selectively outputs the reference voltage to be compared with the output of the integration circuit 41 when stopping the light emission of the xenon tube 3 and the reference voltage to be compared with the output of the integration circuit 41 when resetting the integration capacitor 40. More specifically, the D/A converter 47 outputs the voltage corresponding to the input D/A value as the reference voltage.

A D/A value to be input to the D/A converter 47 for outputting the reference voltage for stopping the light emission of the xenon tube 3 may be referred to as a stop D/A value. A D/A value to be input to the D/A converter 47 for outputting the reference voltage for resetting the integration capacitor 40 may be referred to as a reset D/A value. The reset D/A value and the output voltage of the D/A converter 47 corresponding to the reset D/A value correspond to an example of a first reference value. The stop D/A value and the output voltage of the D/A converter 47 corresponding to the stop D/A value correspond to an example of a second reference value. The D/A converter 47 corresponds to an example of a reference value generation unit which generates a first reference value when the number of times of integration by the integration unit is less than a predetermined number of times and generates a second reference value when the number of times of integration by the integration unit reaches the predetermined number of times.

The output of the D/A converter 47 is connected to an output of the operational amplifier 45 and an input of the comparator 46, and the comparator 46 performs the comparison between the output voltage of the integration circuit 41 and the output voltage of the D/A converter 47. In other words, the comparator 46 corresponds to an example of a comparison unit which compares the integration value by the integration unit with the first reference value. Further, the comparator 46 corresponds to an example of a comparison unit which compares the integration value by the integration unit with the second reference value.

The output voltage of the integration circuit 41 and the output voltage of the D/A converter 47 are input to the comparator 46. The output of the comparator 46 is connected to the CPU 29. When the output voltage of the integration circuit is smaller than the output voltage of the D/A converter 47, for example, a signal Hi is output from the comparator 46. When the output voltage of the integration circuit 41 is larger than the output voltage of the D/A converter 47, for example, a signal Low is output from the comparator 46. The voltage output from the comparator 46 may be set in such a manner that a signal Low is output when the output voltage of the integration circuit 41 is smaller than the output voltage of the D/A converter 47 and a signal Hi is output when the output voltage of the integration circuit 41 is larger than the output voltage of the D/A converter 47.

Figure 3:
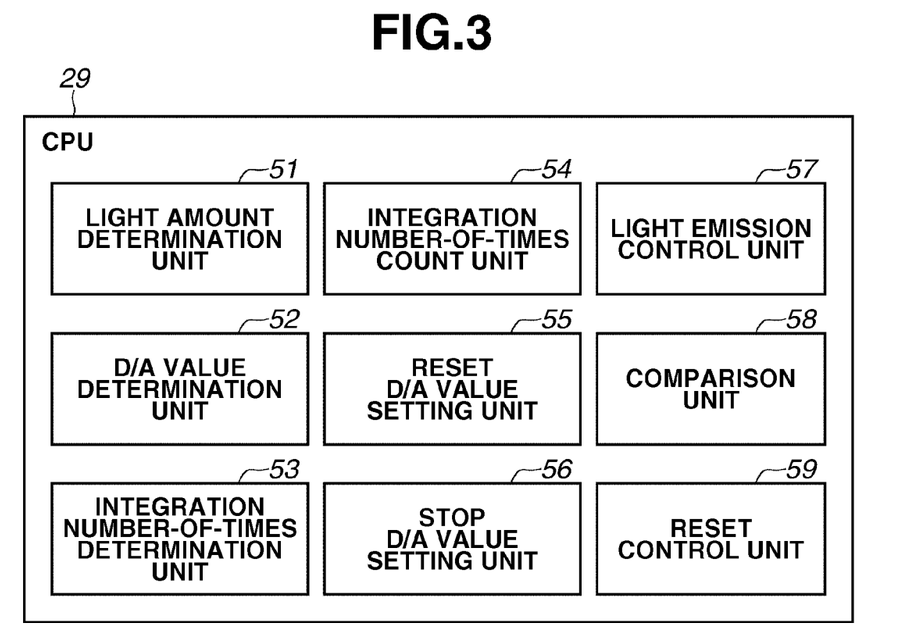
FIG. 3 schematically illustrates an example of a function of a central processing unit (CPU).

FIG. 3 schematically illustrates the function of the CPU 29. The CPU 29 serves as a light amount determination unit 51, a D/A value determination unit 52, an integration number-of-times determination unit 53, an integration number-of-times count unit 54, a reset D/A value setting unit 55, a stop D/A value setting unit 56, a light emission control unit 57, a comparison unit 58, and a reset control unit 59 by executing a program recorded in a memory (not illustrated).

The light amount determination unit 51 determines the light emission amount of the xenon tube 3 based on the imaging mode input via the operation unit 30. In other words, the light amount determination unit 51 determines the amount of light irradiated from the xenon tube 3 to the subject's eye E based on the imaging mode. In addition, the light amount determination unit 51 determines the amount of light irradiated from the xenon tube 3 to the subject's eye E based on the imaging mode and a light amount adjustment value. The imaging mode includes, for example, a mode such as an autofluorescence imaging mode, a color imaging mode, or the like. More specifically, the light amount determination unit 51 determines the light amount based on a table in which the imaging mode and the necessary light amount are correlated with each other.

Figure 4:
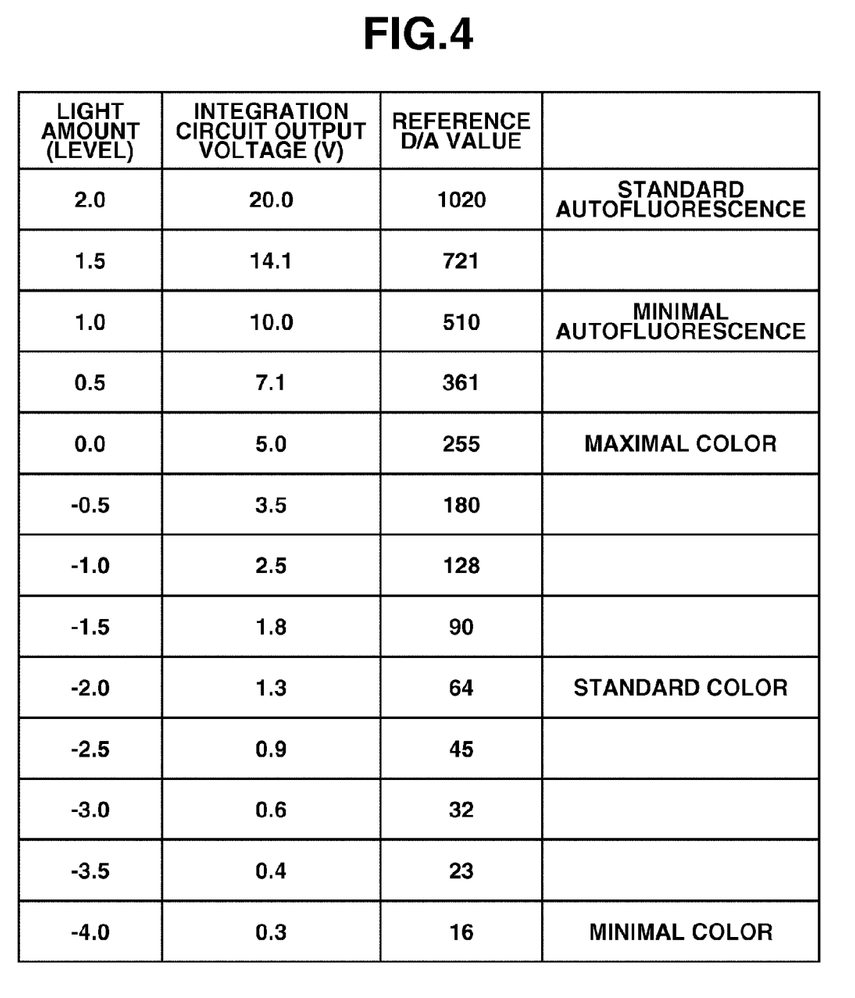
FIG. 4 illustrates an example of a table of relation among a light emission amount, an integration circuit output voltage, and a digital-to-analog (D/A) value.

An example of the table is illustrated in FIG. 4. In the table in FIG. 4, the imaging modes are correlated with the light amount necessary for respective imaging modes. In FIG. 4, the unit of the light amount is described as a "level". The "level" indicates that the light amount of the Level 0 is used as a reference light amount, and the light amount becomes twice the reference light amount when the light amount increases by one level. Also, the "level" indicates that the light amount becomes a half of the reference light amount when the light amount decreases by one level. In the following description, the unit of the light amount is referred to as the "level". In the example illustrated in FIG. 4, the maximum light amount in the color imaging mode is set to Level 0.

The table illustrated in FIG. 4 will be described specifically. In the table illustrated in FIG. 4, the light emission amount of the xenon tube 3 when adjusting the light amount by the unit of Level ½ is correlated with the output voltage of the integration circuit 41, the reference D/A value as the value of the signal input to the D/A converter 47, and the imaging mode.

The table illustrated in FIG. 4 corresponds to the case where the input signal is 8 bit when the range of the output voltage of the D/A converter 47 is from 0 to 5 V, that is, the D/A converter 47 which outputs 5 V when the reference D/A value is 255 is used. The reference D/A value is a digital value which is input to the D/A converter 47. In a case where the output of the D/A converter 47 is an ideal D/A converter which is not restricted by the power supply voltage or the like, when the reference D/A value illustrated in FIG. 4 is input, the integration circuit output voltage corresponding to the reference D/A value illustrated in FIG. 4 is output from the D/A converter 47. For example, the D/A converter 47 outputs 20 V when the reference D/A value is 1020. The reference D/A value is not limited to the value illustrated in FIG. 4.

The table is not limited to the table illustrated in FIG. 4. For example, instead of dividing by Level ½, the light amount may be divided by the narrower level or the wider level. For example, the light amount may be divided by Level ¼ or Level 1. In the table illustrated in FIG. 4, the maximum light amount in the color imaging mode is set to Level 0, however the present invention is not limited thereto. The light amount in a standard color imaging mode may be set to Level 0, that is, the light amount in the other cases may be set to Level 0.

The table illustrated in FIG. 4 includes the integration circuit output voltage which represents the output voltage of the integration circuit 41 corresponding to the light amount, however the present invention is not limited thereto. For example, the table may not include the integration circuit output voltage. In the table illustrated in FIG. 4, the unit of the light amount is described as the "level", but the present invention is not limited thereto. For example, the other units may be used. In the example illustrated in FIG. 4, the light amount becomes twice the reference light amount when the light amount increases by Level 1, but the present invention is not limited thereto. Setting of the light amount can be changed, such that when the light amount increases by Level 1, the light amount may be three times the reference light amount. Similarly, in the example illustrated in FIG. 4, the light amount becomes ½ times the reference light amount when the light amount decreases by Level 1, but the present invention is not limited thereto. The setting of the light amount can be changed, such that when the light amount increases by Level 1, the light amount may become ⅓ times the reference light amount.

For example, when the color imaging mode is selected via the operation unit 30, the light amount determination unit 51 determines the light amount as Level −2 by referring to the table. For example, when the color imaging mode is selected and the light amount adjustment value of Level +2 is input by the operation unit 30, the light amount determination unit 51 determines the light amount as Level 0.

The D/A value determination unit 52 determines the reference D/A value as the value of the signal input to the D/A converter 47 based on the light amount determined by the light amount determination unit 51. More specifically, the D/A value determination unit 52 determines the reference D/A value by referring to the table in FIG. 4. For example, when the light amount is determined as Level 1 by the light amount determination unit 51, the D/A value determination unit 52 determines the reference D/A value as 510. The operation of the D/A value determination unit 52 is not limited thereto. For example, the reference D/A value may be directly determined based on the imaging mode input via the operation unit 30 or the imaging mode and the light amount adjustment value without using the light amount determined by the light amount determination unit 51.

The integration number-of-times determination unit 53 determines the number of times of integration by the integration circuit 41 necessary for measuring the light amount determined by the light amount determination unit 51. The number of times of integration indicates the number of times of reversing (changing) of the output of the comparator 46 when the output of the integration circuit 41 exceeds the reference voltage output from the D/A converter 47 from the state where the integration capacitor 40 is reset. In other words, the number of times of integration indicates the number of times in which the output of the integration circuit 41 exceeds the reference voltage output from the D/A converter 47 from the state where the integration capacitor 40 is reset.

For example, when the light amount is determined as Level 1 by the light amount determination unit 51 and the D/A value is determined as 510 by the D/A value determination unit 52, the integration number-of-times determination unit 53 divides the reference D/A value determined by the D/A value determination unit 52 by 255, which is the input in the case of the maximum output of the D/A converter 47. Here, the integration number-of-times determination unit 53 determines the number of times of integration as two times. When there is a remainder as the result of the division, the integration number-of-times determination unit 53 adds one time to the number of times of integration. Although the reference D/A value determined by the D/A value determination unit 52 is divided by 255, which is the input in the case of the maximum output of the D/A converter 47, the present invention is not limited thereto. For example, the reference D/A value determined by the D/A value determination unit 52 may be divided by the value other than 255. In other words, the integration number-of-times determination unit 53 corresponds to an example of an integration number-of-times determination unit which determines the number of times of integration to be executed by the integration unit based on the light amount determined by the light amount determination unit and the first reference value.

The integration number-of-times count unit 54 counts the number of times of integration. More specifically, the integration number-of-times count unit 54 counts the number of times of reversing of the output of the comparator 46 due to the output of the integration circuit 41 exceeding the reference voltage output from the D/A converter 47.

The reset D/A value setting unit 55 sets the D/A value to the D/A converter 47. More specifically, the value which is used to divide the reference D/A value by the integration number-of-times determination unit 53 is set (input) to the D/A converter 47. For example, the reset D/A value setting unit 55 inputs 255, which is the maximum D/A value to be input to the D/A converter 47, to the D/A converter 47.

The comparison unit 58 compares the number "count" of times of integration counted by the integration number-of-times count unit 54 with the number N of times of integration determined by the integration number-of-times determination unit 53.

The stop D/A value setting unit 56 sets the D/A value to the D/A converter 47. More specifically, when a difference obtained by the comparison unit 58 between the number of times of integration counted by the integration number-of-times count unit 54 and the number of times of integration determined by the integration number-of-times determination unit 53 is 1, the D/A value is set to the D/A converter 47. The D/A value to be set to the D/A converter 47 is the value of the remainder as the result of the division by the integration number-of-times determination unit 53. When the remainder as the result of the division by the integration number-of-times determination unit 53 is zero, the value which is obtained by dividing the reference D/A is set to the D/A converter 47.

The reset control unit 59 resets the output of the integration circuit 41. More specifically, in a case where the output of the comparator 46 is reversed due to the output of the integration circuit 41 exceeding the output of the D/A converter 47, the reset control unit 59 turns on the analog switch 44 so as to discharge the electric charges of the integration capacitor 40, thereby resetting the output of the integration circuit 41. In a case where the output of the comparator 46 is reversed due to the output of the integration circuit 41 falling below the output of the D/A converter 47 with the resetting of the output of the integration circuit, the reset control unit 59 turns off the analog switch 44.

The reset control unit 59 turns on the analog switch 44 by outputting a Hi signal to the analog switch 44, and turns off the analog switch 44 by outputting a Low signal to the analog switch 44. As the analog switch 44, a switch may be used which is turned off when receiving a Hi signal and is turned on when receiving a Low signal.

The light emission control unit 57 controls the light emission of the xenon tube 3. When an operator starts an imaging operation using the operation unit 30, the light emission control unit 57 starts the light emission of the xenon tube 3 by setting the Xe_ON signal to Hi so that the IGBT 32 is turned on. When the number "count" of times of integration counted by the integration number-of-times count unit 54 is equal to the number N of times of integration determined by the integration number-of-times determination unit 53 as a result of the comparison by the comparison unit 58, the light emission control unit 57 stops the light emission of the xenon tube 3 by setting the Xe_ON signal to Low so that the IGBT 32 is turned off. In other words, the light emission control unit 57 corresponds to an example of a light emission control unit which controls the light emission of the light source.

Figure 5:
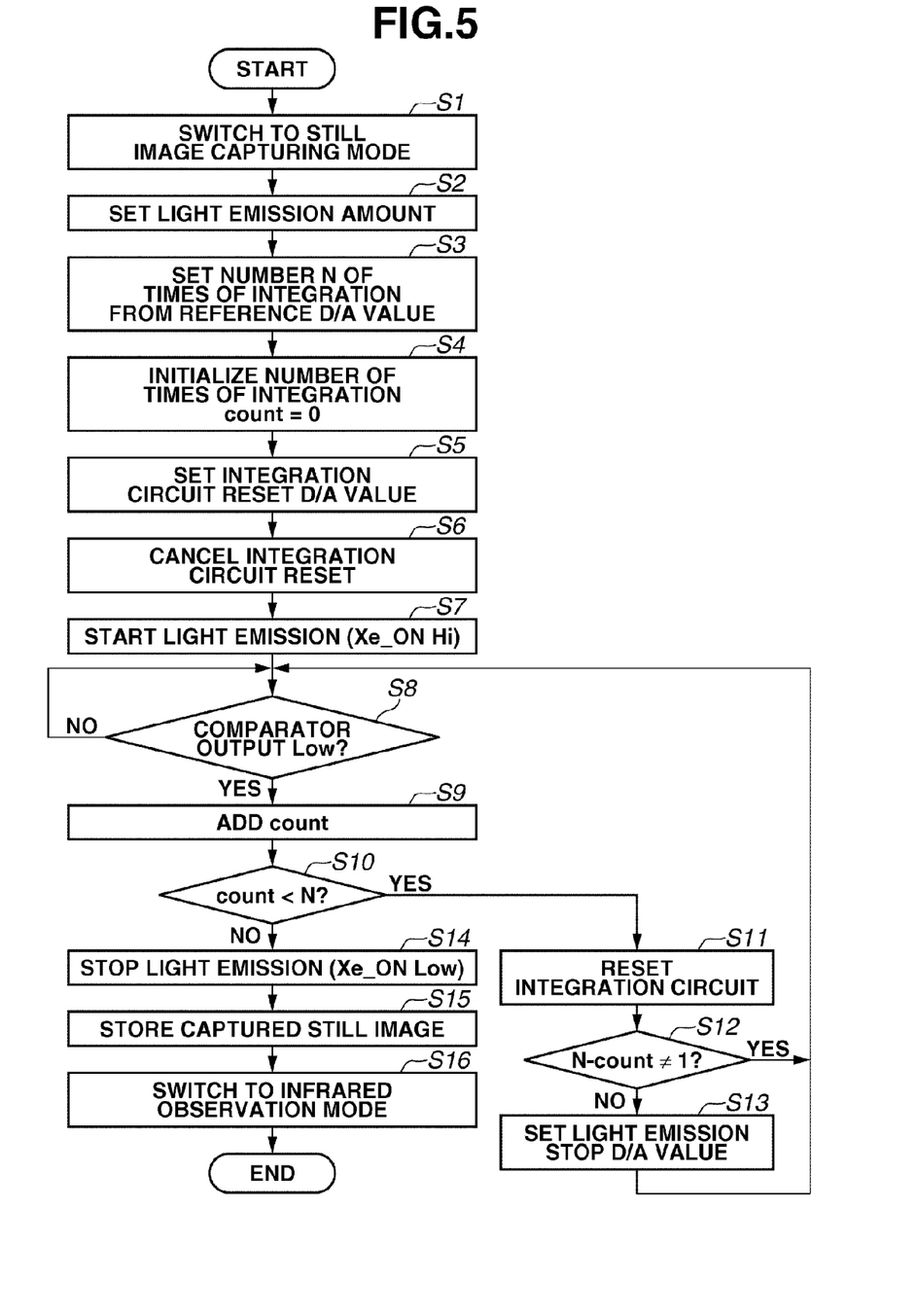
FIG. 5 is a flowchart illustrating an example of an operation of the light amount detection unit.

Next, operations from the start of the imaging operation to the stop of the light emission of the xenon tube 3 will be described by referring to a flowchart illustrated in FIG. 5.

First, it is assumed that an operator operates a mode switch (not illustrated) of the operation unit 30 so as to select a color imaging mode or an autofluorescence imaging mode. When the color imaging mode is selected, the CPU 21 retracts the autofluorescence imaging excitation filter 48 from the optical axis. The operator operates a light amount adjustment switch (not illustrated) of the operation unit 30 so as to set the light amount adjustment value during the imaging operation. These operations may be performed during or after an alignment or a focus operation to be described below.

Next, the alignment between the fundus camera and the subject's eye E is performed using a fundus image of the subject's eye E, which is illuminated by the infrared LED 1 of the infrared observation light source and is displayed on the display unit 20, and an aligning index image, which is projected to a cornea of the subject's eye E by the infrared LED 22 of the aligning index light source. The focus operation is performed using an index image of the infrared LED 14 of the focusing index light source. When the alignment and the focus operation are completed, the operator starts the imaging operation by pressing an imaging switch (not illustrated) of the operation unit 30.

In step S1, when the imaging switch is pressed, the CPU 29 turns off the infrared LED 1, the infrared LED 22, and the infrared LED 14 and retracts the focusing index projection optical system O3 from the optical axis of the illumination optical system O1 in order to switch from the infrared observation mode to the still imaging mode. Further, the CPU 21 inserts the autofluorescence imaging inhibition filter 49 into the optical axis when the autofluorescence imaging mode is selected.

In step S2, the light amount determination unit 51 determines the light emission amount from the set imaging mode and the light amount correction value. For example, the imaging light amount becomes Level +1.5 in the case of the correction of Level −0.5 in the autofluorescence imaging mode.

In step S3, the integration number-of-times determination unit 53 determines the number N of times of integration. First, the D/A value determination unit 52 determines the reference D/A value from the table in FIG. 4 based on the level number of the light amount which is determined by the light amount determination unit 51. Since the current light emission amount is Level +1.5, the integration circuit output voltage is 14.1 V, and the reference D/A value at this time becomes 721.

Next, the integration number-of-times determination unit 53 divides the reference D/A value determined by the D/A value determination unit 52 by 255 since the maximum setting value of the D/A converter 47 is 255. Then, the remainder of 211 is obtained after calculating the equation of 721/255=2. Thus the number N of times of integration is the quotient of 2, and 1 is further added to N when there is the remainder as the division result. Accordingly, the integration number-of-times determination unit 53 determines the number N of times of integration as 3. In other words, when the integration to the D/A value 255=5 V is performed twice and the integration to the D/A value 211=4.1 V is performed once, this operation is equivalent to the case where the integration to the integration circuit output voltage of 14.1 V is performed. The integration number-of-times determination unit 53 may not use the digital value, and may obtain the number of times of integration by dividing 14.1 V by 5 V.

In step S4, the value "count" which represents the number of times of integration counted by the integration number-of-times count unit 54 is initialized to 0.

In step S5, the reset D/A value setting unit 55 sets the D/A value for resetting the integration circuit to 255 as the maximum value. In other words, the reset D/A value setting unit 55 inputs the digital value of 255 to the input of the D/A converter 47.

In step S6, the CPU 29 turns off the analog switch 44 and cancels the reset of the integration circuit.

In step S7, the light emission control unit turns on the IGBT 32 by setting the Xe_ON signal to Hi. When the IGBT 32 is turned on, a trigger signal is applied to the xenon tube 3, so that the light emission is started.

In step S8, the CPU 29 waits until the output of the comparator 46 becomes Low. When the output becomes Low (YES in step S8), the processing proceeds to step S9.

In step S9, when the output of the comparator 46 becomes Low, the integration number-of-times count unit 54 adds 1 to the "count".

In step S10, the comparison unit 58 compares the number N of times of integration set in step S3 with the number "count" of times of integration counted by the integration number-of-times count unit 54. When the count is less than N (YES in step S10), the processing proceeds to step S11.

In step S11, the reset control unit 59 turns on the analog switch 44 for a time which is sufficiently short with respect to the light emission time and once resets (initializes) the output of the integration circuit. When the analog switch 44 is turned on, the electric charges accumulated in the integration capacitor 40 are discharged, and the voltage of the integration circuit becomes 0 V, so that the output of the comparator 46 returns to Hi. In other words, the analog switch 44 functions as an example of an initialization unit which initializes the integration value when the integration value exceeds the first reference value as the comparison result by the comparison unit.

In step S12, the comparison unit 58 determines whether "N−count≠1" by comparing the number N of times of integration determined by the integration number-of-times determination unit 53 with the number "count" of times of integration counted by the integration number-of-times count unit 54. In the case where N−count≠1 (YES in step S12), the processing returns to step S8, and the processing from step S8 to step S12 are repeated until "N−count=1" is satisfied. In the case where N−count=1 (NO in step S12), the processing proceeds to step S13.

In step S13, the stop D/A value setting unit 56 sets the D/A value for stopping the light emission of the xenon tube 3 to the D/A converter 47. The setting value at this time is set as the remainder of 211 of the division in step S3.

When the processing in step S13 is ended, the processing returns to step S8, and the processing from step S8 to step S10 are performed again. In other words, the comparison unit compares the integration value by the integration unit with the second reference value when the number of times of integration by the integration unit becomes a predetermined number (N−1) of times. The predetermined number is a value which is obtained by subtracting 1 from the number of times of integration to be performed by the integration unit, which is determined by the integration number-of-times determination unit. In step S10, when it is determined as "count=N" (NO in step S10), the processing proceeds to step S14.

In step S14, the light emission control unit 57 stops the light emission of the xenon tube 3 by setting the Xe_ON signal to Low so that the IGBT 32 is turned off. In other words, the light emission control unit stops the light emission of the light source when the integration value by the integration unit exceeds the second reference value as the comparison result by the comparison unit.

After the stop of the light emission of the xenon tube 3, in step S15, the image signal processing unit 19 generates a still image corresponding to the imaging mode from the output of the imaging unit 17, and the CPU 29 stores the still image in the recording unit 31. Then, in step S16, the still imaging mode is switched to the infrared observation mode by the control of the CPU 29.

The operations from the light emission in step S7 to the stop of the light emission in step S14 will be described by referring to a timing chart in FIG. 6.

Figure 6:
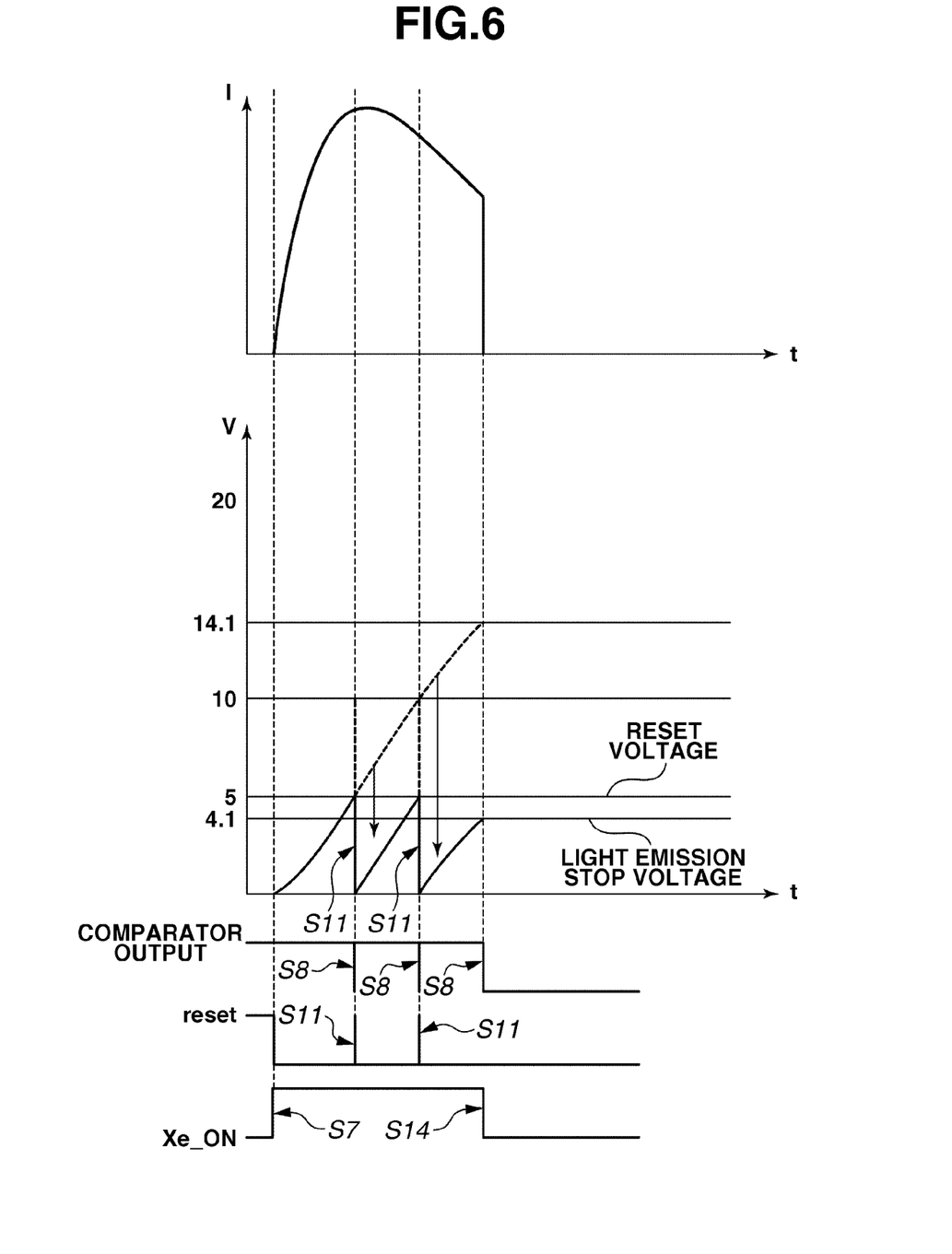
FIG. 6 is a timing chart illustrating an example in which the light emission starts and stops.

FIG. 6 illustrates a change with time of the light amount and the output voltage of the integration circuit. In the example illustrated in FIG. 6, the number N of times of integration is 3 and the reset D/A value is 255 (5 V). In addition, the number "count" of times of integration is zero (count=0) in the initial state.

As described above, in step S7, when the light emission control unit 57 turns the Xe_ON signal to Hi, the xenon tube 3 starts to emit light. In step S8, when the output of the comparator 46 becomes Low (the integration circuit output voltage=5 V), then in step S9, the "count" will be 1, however, "count<N" is satisfied. Accordingly, in step S11, the output of the integration circuit is reset, and the output of the comparator 46 returns to Hi (the integration circuit output=0 V).

Similarly, when the output of the comparator 46 becomes Low (the integration circuit output voltage=5 V) in subsequent step S8, the "count" will be in step S9. However, "count<N" is satisfied. Accordingly, in step S11, the output of the integration circuit is reset, and the output of the comparator 46 returns to Hi (the integration circuit output=0 V). At this time, "N−count=1" is satisfied, thus in step S13, the stop D/A value setting unit 56 sets the D/A value 211 (4.1 V) to the D/A converter 47.

When the output of the comparator 46 becomes Low (the integration circuit output voltage=4.1 V) in subsequent step S8, the "count" will be 3 in step S9, so that "count=N" is satisfied. Accordingly, in step S14, the control unit turns the Xe_ON signal to Low, so that the light emission of the xenon tube 3 is stopped.

Originally, the light emission of the xenon tube 3 needs to be stopped when the output of the integration circuit becomes 14.1 V. However, since the comparator 46 may perform the comparison only to 5 V, when the integration to 5 V is performed twice and the integration to 4.1 V is performed once, 5 V×2+4.1 V=14.1 V, and this operation is equivalent to the case where the integration to 14.1 V is performed, thereby obtaining the target light emission amount.

Figure 7:
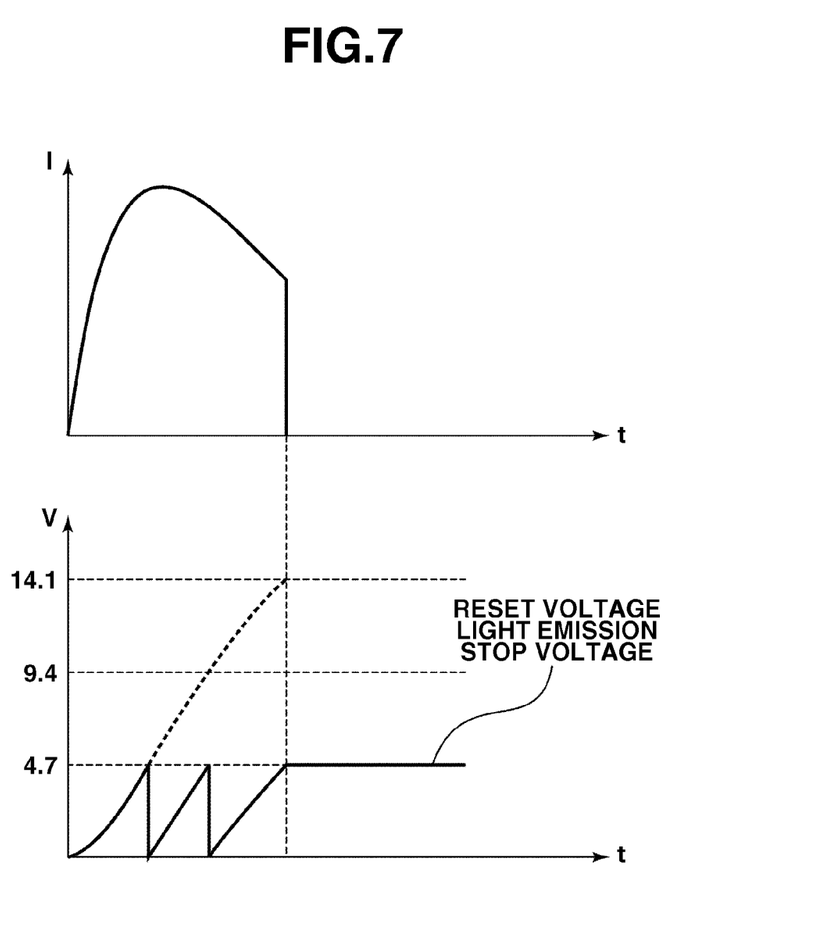
FIG. 7 is a timing chart illustrating an example in which the light emission starts and stops when a reset reference value and a light emission stop reference value are equal to each other.

The described technique is not limited to the above-described exemplary embodiment, and may be implemented in various modified forms without departing from the spirit of the present exemplary embodiment For example, in the present exemplary embodiment, the reset D/A value and the light emission stop D/A value are different values, that is, the first reference value and the second reference value are different, but the same D/A value may be used. For example, since the output voltage of the integration circuit is 14.1 V in the light emission amount in the present exemplary embodiment, 14.1 V/3=4.7 V is satisfied. Accordingly, when the integration to 4.7 V is performed three times, this operation is equivalent to the case where the integration to 14.1 V is performed. In this case, the integration number-of-times determination unit 53 determines the number of times of integration by dividing the reference D/A value of 721 determined by the D/A value determination unit 52 by a value equal to or less than 255 as the input when the D/A converter 47 outputs 5 V so that no remainder is obtained. Accordingly, the reset D/A value setting unit 55 and the stop D/A value setting unit 56 can respectively set the reset D/A value and the stop D/A value, which are equal to each other, to the D/A converter 47. The light emission amount and a waveform of the output voltage of the integration circuit at this time are illustrated in FIG. 7.

A configuration may be adopted in which at least one of the number of times of integration, the reset D/A value, and the stop D/A value can be set via the operation unit 30.

According to the present exemplary embodiment, the observation light source is an LED, but the present invention is not limited thereto. For example, the xenon tube may be used as the observation light source. In this case, the observation light amount may be controlled by providing the xenon tube driving circuit 24 and the light amount detection unit 28 for the xenon tube as the observation light source.

According to the present exemplary embodiment, the light emission amount is determined corresponding to the imaging mode such as the autofluorescence imaging mode or the color imaging mode, but the present invention is not limited thereto. For example, the light emission amount may be determined corresponding to the ISO sensitivity.

According to the present exemplary embodiment, various processes are performed by the CPU 29, but the present invention is not limited thereto. Any device which may attain the above-described function may be used. For example, a field programmable gate array (FPGA) may be used instead of the CPU.

A plurality of integration capacitors 40 may be provided in parallel. For example, the plurality of the integration capacitors 40 having different values may be provided, and the integration of the light emission amount may be determined by selectively using the plurality of the integration capacitors 40 in response to the light amount. More specifically, when the light emission amount is small, the integration capacitor 40 having a large capacitance may be selected from the plurality of the integration capacitors 40, accordingly the output of the integration circuit 41 may be prevented from being degraded even when the light emission amount is small. Since the degradation in the output of the integration circuit 41 may be prevented, the degradation in the reference voltage may be also prevented. Accordingly, the output of the integration circuit 41 or the reference voltage is hardly affected by noise, and the light emission amount may be adjusted with high precision. In order to select an arbitrary capacitor from the plurality of the integration capacitors 40, for example, a switch may be provided between the integration capacitor 40 and the integration circuit 41.

Figure 8:
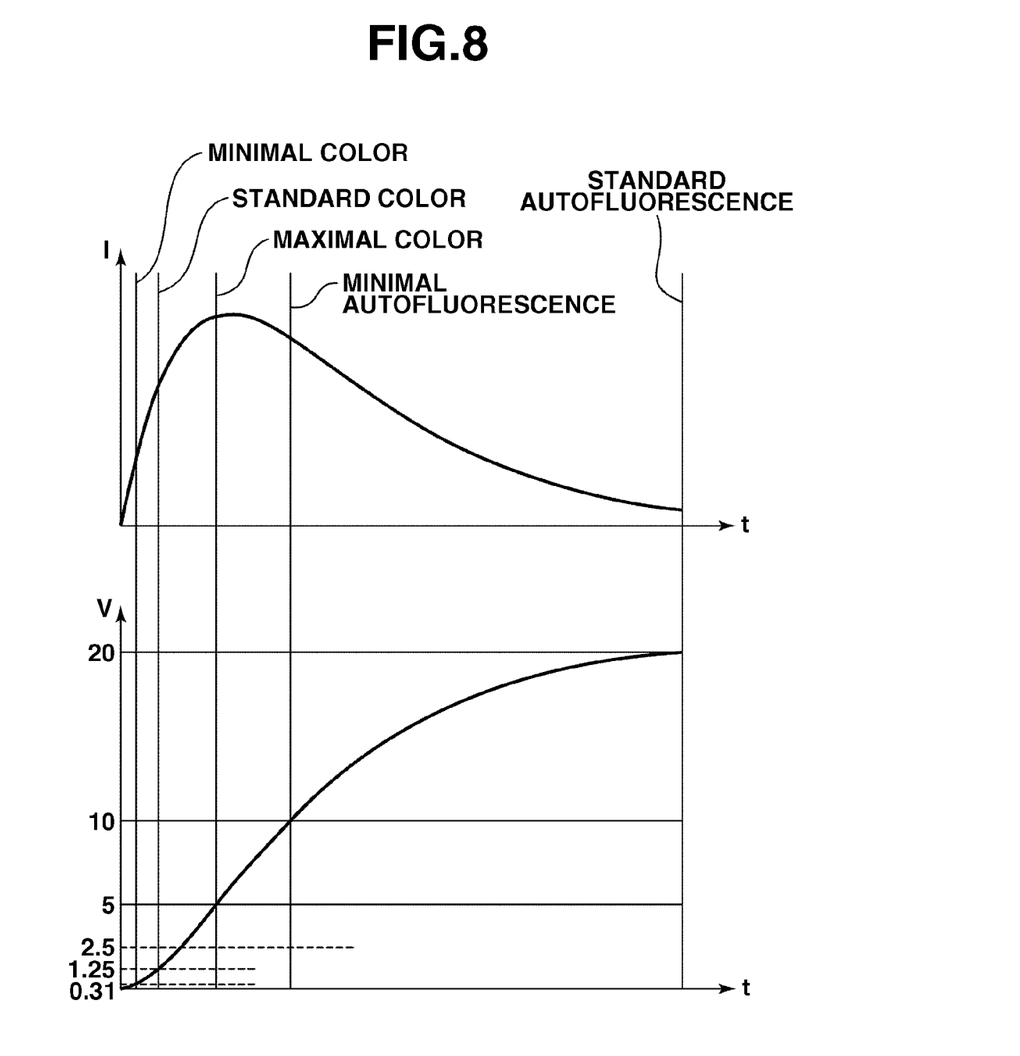
FIG. 8 illustrates an example of relation between a light emission amount and an output voltage of an integration circuit.

In order to describe the effect of the ophthalmologic apparatus according to aspects of the present invention, there is illustrated a relation between the light emission amount of the xenon tube 3 and the output voltage of the integration circuit when the integration circuit is not reset. FIG. 8 is a graph illustrating the relation between the light emission amount of the xenon tube 3 and the output voltage of the integration circuit 41. An upper part of the graph illustrates a photoelectric current which flows to the photodiode 39 in proportion to the light amount of the xenon tube 3. A lower part of the graph illustrates the output voltage of the integration circuit 41 when the photoelectric current flowing to the photodiode 39 is integrated by the integration circuit. It is assumed that the output voltage range of the D/A converter is 0 to 5 V.

When it is assumed that the light amount correction range in the color imaging mode is Level ±2 of the standard light amount, the maximum light amount in the color imaging mode is obtained at the correction of Level +2 of the standard light amount. When the capacitance of the integration capacitor 40 is determined so that the output voltage of the integration circuit 41 becomes 5V at the maximum light amount in the color imaging mode, the maximum light emission amount in the necessary color imaging mode is obtained if the current of the xenon tube 3 is interrupted when the output of the integration circuit 41 exceeds 5 V.

Since the standard light amount in the color imaging mode is ¼ (Level −2) of the maximum light amount, the necessary light emission amount which interrupts the current of the xenon tube 3 is obtained when the output voltage of the integration circuit 41 becomes 1.25 V.

Since the minimum light amount in the color imaging mode is obtained at the correction of Level −2 of the standard light amount and is ¼ (Level −2) of the standard light amount, the minimum light emission amount is obtained when the current of the xenon tube 3 is interrupted when the output of the integration circuit 41 is about 0.31 V. When it is assumed that the standard light amount in the autofluorescence imaging mode needs eight times (Level +4) the light amount in the color imaging mode, the standard light amount becomes four times the maximum light amount in the color imaging mode, and the output of the integration circuit becomes 20 V. At this time, since the output of the integration circuit exceeds the maximum output of the D/A converter 47, the comparison by the comparator 46 may not be performed. In FIG. 8, when the light amount exceeds the maximum light amount in the color imaging mode, the output of the integration circuit exceeds the maximum output of the D/A converter 47, so that the light amount may not be controlled.

In contrast, when the capacitance of the integration capacitor is set to be large so that the output of the integration circuit becomes 5 V based on the light amount necessary for the autofluorescence, the minimum light amount in the color imaging mode becomes 1/64 (Level −6) of the light amount in the autofluorescence imaging mode, and the output of the integration circuit becomes about 78 mV which is a very small value compared to 5 V. For this reason, the resolution of the reference voltage degrades around the minimum light amount and the precision in the light amount control degrades. In addition, when the voltage is low, the influence of noise more frequently occurs.

A method may be adopted in which an optical light amount restriction member such as a filter is provided in front of the photodiode according to the imaging mode, however, a switching mechanism is needed, and the apparatus increases in cost and becomes complicated.

In this way, according to aspects of the ophthalmologic apparatus of the present invention, even when the output voltage of the integration circuit exceeds the maximum value of the reference voltage for stopping the light emission, the integration circuit may be reset during the light emission of the xenon tube and the light emission amount may be adjusted by performing the integration in a plurality of times. In other words, according to aspects of the ophthalmologic apparatus of the present invention, the light amount may be adjusted regardless of the relation between the reference voltage and the output of the integration circuit.

Further, according to aspects of the ophthalmologic apparatus of the present invention, since the integration capacitor does not need to be increased in capacitance according to the case where the large light amount is necessary for the imaging light amount, it is possible to prevent the resolution of the reference voltage from being degraded and prevent the precision in the light amount control from being degraded.

Further, according to aspects of the ophthalmologic apparatus of the present invention, since the switching mechanism is not needed, it is possible to prevent the apparatus from increasing in cost and being complicated.

Aspects of the present invention can also be realized by a computer of a system or apparatus (or devices such as a CPU or a micro-processing unit (MPU)) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-167052 filed Jul. 29, 2011, which is hereby incorporated by reference herein in its entirety.

What is claimed is:

1. An ophthalmologic apparatus comprising:
   an integration unit configured to integrate a light emission amount of a light source for illuminating a subject's eye;
   a comparison unit configured to compare an integration value indicating a light emission amount of the light source integrated by the integration unit with a predetermined reference value;
   a resetting unit configured to reset the integration value if a first integration value indicating a light emission amount of the light source exceeds a first reference value as a result of comparing the first integration value with the first reference value; and
   a light emission control unit configured to control light emission of the light source,
   wherein the comparison unit is configured to compare a second integration value indicating an integrated light emission amount of the light source after the integration value is reset by the resetting unit with a second reference value,
   wherein the light emission control unit is configured to stop the light emission of the light source if the second integration value exceeds the second reference value as a result of comparing the second integration value with the second reference value, and
   wherein the first reference value and second reference value are different values.

2. The ophthalmologic apparatus according to claim 1, wherein the comparison unit compares the second integration value with the second reference value if the number of times of integration by the integration unit indicating a number of times the integration value exceeds the predetermined reference value becomes a predetermined number of times.

3. The ophthalmologic apparatus according to claim 2, further comprising:
   a light amount determination unit configured to determine a light amount for illuminating the subject's eye; and
   an integration number-of-times determination unit configured to determine the number of times of integration to be performed by the integration unit based on the first reference value and the light amount determined by the light amount determination unit.

4. The ophthalmologic apparatus according to claim 3, wherein the predetermined number of times is a value which is obtained by subtracting one from the number of times of integration to be performed by the integration unit and determined by the integration number-of-times determination unit.

5. The ophthalmologic apparatus according to claim 2, further comprising a reference value generation unit configured to generate the first reference value if the number of times of integration by the integration unit is less than the predetermined number of times and generate the second reference value if the number of times of integration by the integration unit becomes the predetermined number of times.

6. The ophthalmologic apparatus according to claim 1,
   wherein the integration unit includes a photodiode which generates a current corresponding to the light emission amount of the light source, and
   wherein the photodiode is provided on an optical axis of the light source in a direction opposite to a direction directed from the light source toward the subject's eye with reference to the light source.

7. The ophthalmologic apparatus according to claim 1, wherein the light emission control unit is configured to not stop the light emission of the light source during a period after the first integration value is compared with the first reference value and before the second integration value exceeds the second reference value.

8. The ophthalmologic apparatus according to claim 1, wherein the second reference value is smaller than the first reference value.

9. The ophthalmologic apparatus according to claim 1, wherein the first reference value is equal to the second reference value.

10. The ophthalmologic apparatus according to claim 6, further comprising:
   a member including a reflective surface for reflecting light emitted by the light source and transmission portion,
   wherein the photodiode is configured to receive the light emitted by the light source via the transmission portion, and
   wherein the member is provided in a direction opposite to a direction in which the light emitted by the light source travels toward the subject's eye with reference to the light source.

11. An ophthalmologic method comprising:
   integrating a light emission amount of a light source for illuminating a subject's eye;
   comparing an integration value indicating a light emission amount of the light source with a predetermined reference value;
   resetting the integration value if a first integration value indicating a light emission amount of the light source exceeds a first reference value as a result of comparing the first integration value with the first reference value; and
   controlling light emission of the light source,
   wherein comparing the integration value includes comparing a second integration value indicating an integrated light emission amount of the light source after the integration value is reset by the resetting unit with a second reference value,
   wherein controlling light emission of the light source includes stopping the light emission of the light source if the second integration value exceeds the second reference value as a result of comparing the second integration value with the second reference value, and
   wherein the first reference value and second reference value are different values.

12. A non-transitory computer readable medium comprising program code to cause an ophthalmologic apparatus to perform an ophthalmologic method comprising:
   integrating a light emission amount of a light source for illuminating a subject's eye;
   comparing an integration value indicating a light emission amount of the light source with a predetermined reference value;
   resetting the integration value if a first integration value indicating a light emission amount of the light source exceeds a first reference value as a result of comparing the first integration value with the first reference value; and
   controlling light emission of the light source,
   wherein comparing the integration value includes comparing a second integration value indicating an integrated light emission amount of the light source after the integration value is reset by the resetting unit with a second reference value,
   wherein controlling light emission of the light source includes stopping the light emission of the light source if the second integration value exceeds the second reference value as a result of comparing the second integration value with the second reference value, and
   wherein the first reference value and second reference value are different values.

13. An ophthalmologic apparatus comprising:
   an integration unit configured to integrate a light emission amount of a light source for illuminating a subject's eye;
   a comparison unit configured to compare an integration value indicating a light emission amount of the light source integrated by the integration unit with a predetermined reference value;
   a resetting unit configured to reset the integration value based on a result of comparing a first integration value indicating a light emission amount of the light source with the first reference value; and
   a light emission control unit configured to control light emission of the light source,
   wherein the comparison unit is configured to compare a second integration value indicating an integrated light emission amount of the light source after the integration value is reset by the resetting unit,
   wherein the light emission control unit is configured to reduce the light emission amount of the light source based on a result of comparing the second integration value with the second reference value,
   wherein the first reference value and second reference value are different values.

14. The ophthalmologic apparatus according to claim 13, wherein the light emission control unit is configured to stop the light emission of the light source based on a result of comparing the second integration value with the second reference value.

15. The ophthalmologic apparatus according to claim 14, wherein the light emission control unit is configured to not stop the light emission of the light source during a period after the first integration value is compared with the first reference value and before the light emission of the light source is stopped based on the result of comparing the second integration value with the second reference value.

16. An ophthalmologic method comprising:
   integrating a light emission amount of a light source for illuminating a subject's eye;

comparing an integration value indicating a light emission amount of the light source with a predetermined reference value;

resetting the integration value based on a result of comparing a first integration value indicating a light emission amount of the light source with the first reference value; and controlling light emission of the light source, wherein comparing the integration value includes comparing a second integration value indicating an integrated light emission amount of the light source after the integration value is reset by the resetting unit, wherein controlling the light emission of the light source includes reducing the light emission amount of the light source based on a result of comparing the second integration value with the second reference value, and wherein the first reference value and second reference value are different values.

17. A non-transitory computer readable medium comprising program code to cause an ophthalmologic apparatus to perform an ophthalmologic method comprising:

integrating a light emission amount of a light source for illuminating a subject's eye;

comparing an integration value indicating a light emission amount of the light source with a predetermined reference value;

resetting the integration value based on a result of comparing a first integration value indicating a light emission amount of the light source with the first reference value; and controlling light emission of the light source, wherein comparing the integration value includes comparing a second integration value indicating an integrated light emission amount of the light source after the integration value is reset by the resetting unit, wherein controlling the light emission of the light source includes reducing the light emission amount of the light source based on a result of comparing the second integration value with the second reference value, and wherein the first reference value and second reference value are different values.

18. An ophthalmologic apparatus comprising:

an integration unit configured to integrate a light emission amount of a light source for illuminating a subject's eye, the integration unit connecting to a single comparator; and a light emission control unit configured to stop light emission of the light source after it is determined that an integration value indicating a light emission amount of the light source integrated by the integration unit connecting to the single comparator exceeds a predetermined reference value multiple times.

* * * * *